US009683940B2

(12) United States Patent
Hosoi et al.

(10) Patent No.: US 9,683,940 B2
(45) Date of Patent: *Jun. 20, 2017

(54) PARTICLE DETECTING AND DISCRIMINATING DEVICE AND METHOD

(71) Applicant: Azbil Corporation, Tokyo (JP)

(72) Inventors: Tomoki Hosoi, Tokyo (JP); Daisuke Obara, Tokyo (JP); Masashi Furuya, Tokyo (JP); Seiichirou Kinugasa, Tokyo (JP)

(73) Assignee: AZBIL CORPORATION, Tokyo (JP)

( * ) Notice: Subject to any disclaimer, the term of this patent is extended or adjusted under 35 U.S.C. 154(b) by 83 days.

This patent is subject to a terminal disclaimer.

(21) Appl. No.: 14/750,125

(22) Filed: Jun. 25, 2015

(65) Prior Publication Data

US 2015/0377786 A1    Dec. 31, 2015

(30) Foreign Application Priority Data

Jun. 26, 2014 (JP) ................ 2014-131842

(51) Int. Cl.
  *G01N 21/64* (2006.01)
  *G01N 15/14* (2006.01)
  *G01J 1/42* (2006.01)

(52) U.S. Cl.
  CPC ............ *G01N 21/6486* (2013.01); *G01J 1/42* (2013.01); *G01N 15/14* (2013.01);
  (Continued)

(58) Field of Classification Search
  CPC ........ G01N 21/6486; G01N 2015/1486; G01J 1/42
  (Continued)

(56) References Cited

U.S. PATENT DOCUMENTS 7,060,992 B1    6/2006 Barney
7,295,319 B2   11/2007 Kajii
(Continued)

FOREIGN PATENT DOCUMENTS

JP    H08-29331 A    2/1996
JP   2003-139707 A   5/2003
(Continued)

OTHER PUBLICATIONS

Hasegawa, N. et al., Instantaneous Bioaerosol Detection Technology and Its Application, azbil Technical Review, 2-7, Yamatake Corporation, Dec. 2009.
Thornton, Joel A. et al., "Atmospheric NO2: In Situ Laser-Induced Fluorescence Detection at Parts per Trillion Mixing Ratios," Analytical Chemistry, vol. 72, No. 3, Feb. 2000, pp. 528-539.
Nizkorodov, S. A. et al., "Time-resolved fluorescence of NO2 in a magnetic field," vol. 215, No. 6, Chemical Physics Letters, Dec. 17, 1993, pp. 662-667.
(Continued)

*Primary Examiner* — Que T Le
(74) *Attorney, Agent, or Firm* — Troutman Sanders LLP

(57) ABSTRACT

A particle detecting device includes: a light measuring instrument that measures measured values for intensities of first, second, and third lights of mutually differing wavelengths, produced by particles to be measured; a boundary information storing portion that stores a non-linear discriminating boundary for separating a class of a first classification of particles and a class of a second classification of particles; and a particle classifying portion that classifies the particle being measured into either of the classifications for the first and second classifications of particles, based on measured values for the intensities of the first through third lights and on the discriminating boundary.

20 Claims, 11 Drawing Sheets

(52) U.S. Cl.
CPC ......... *G01N 2015/1402* (2013.01); *G01N 2015/1477* (2013.01); *G01N 2015/1488* (2013.01)

(58) Field of Classification Search
USPC ....... 250/222.1, 221, 574–576; 356/335–343
See application file for complete search history.

(56) References Cited

U.S. PATENT DOCUMENTS

| 8,717,550 B2* | 5/2014 | Janka | G01N 15/1459 356/335 |
|---|---|---|---|
| 2004/0262501 A1 | 12/2004 | Kajii | |
| 2013/0077087 A1 | 3/2013 | Janka et al. | |

FOREIGN PATENT DOCUMENTS

| JP | 2011-083214 A | 4/2011 |
|---|---|---|
| JP | 2012-086105 A | 5/2012 |

OTHER PUBLICATIONS

Burges, C. J. C. Ed—Blockeel Hendrik et al: "A tutorial on support vector machines for pattern recognition", Journal of Data Mining and Knowledge Discovery, Norwell, MA, US, vol. 2, No. 2, Jan. 1, 1998 (Jan. 1, 1998), pp. 121-167.

Extended European Search Report dated Oct. 29, 2015, issued in corresponding European Application No. 15173743.4.

* cited by examiner

PARTICLE DETECTING AND DISCRIMINATING DEVICE AND METHOD

CROSS REFERENCE TO RELATED APPLICATION

This application claims priority under 35 U.S.C. §119 to Japanese Patent Application No. 2014-131842, filed on Jun. 26, 2014, the entire content of which being hereby incorporated herein by reference.

FIELD OF TECHNOLOGY

The present disclosure relates to an inspecting technology, and relates to a particle detecting device and particle detecting method.

BACKGROUND

In clean rooms, such as bio clean rooms, airborne microorganism particles and non-microorganism particles are detected and recorded using particle detecting devices. See, for example, Japanese Unexamined Patent Application Publication No. 2011-83214 and N. Hasegawa, et al., *Instantaneous Bioaerosol Detection Technology and Its Application*, azbil Technical Review, 2-7, Yamatake Corporation, December 2009. The state of wear of the air-conditioning equipment of the clean room can be ascertained from the result of the particle detection. Moreover, a record of particle detection within the clean room may be added as reference documentation to the products manufactured within the clean room. Optical particle detecting devices draw in air from a clean room, for example, and illuminate the drawn-in air with light. If a microorganism particle or non-microorganism particle is included in the air, then the particle that is illuminated by the light will produce fluorescence or scattered light will be produced by the particle. Because of this, it is possible to detect the numbers and sizes of microorganism particles and non-microorganism particles that are included in a gas, through detecting the fluorescent and scattered light. Moreover, a technology able to detect accurately particles in not just clean rooms, but in fluids as well, is desired. See, for example, Japanese Unexamined Patent Application Publication No. H8-29331.

The intensity of fluorescence emitted from particles may differ depending on the type of particle. Moreover, the intensity of scattered light produced by a particle may also differ depending on the type of particle. Because of this, a method has been proposed for identifying whether a particle is a biologic particle or a non-biologic particle based on the intensity of fluorescence and on the intensity of scattered light. See, for example, US Patent Application Publication No. 2013/0077087.

Given this, an aspect of the present disclosure is to provide a particle detecting device and particle detecting method wherein biologic particles and non-biologic particles can be discriminated accurately.

SUMMARY

One aspect of the present invention provides a particle detecting device including: a light measuring instrument that measures measured values of intensities of first, second, and third lights, produced by a particle being measured, with mutually varying wavelengths; a boundary information storing portion that stores a non-linear discriminating boundary for separating a class of particles of a first classification and a class of particles of a second classification; and a particle classifying portion that classifies a particle to be measured into a class for particles of either a first or second classification, based on the measured values for the intensities for the first through third lights and on a discriminating boundary.

In the particle detecting device set forth above: the first and second lights may be lights in the fluorescent band, and the third light may be scattered light. Moreover, one of the particles of the first and second classifications may be a biologic particle, and the other may be a non-biologic particle.

In the particle detecting device, the boundary information storing portion may store a three-dimensional coordinate system including the discriminating boundary. The three-dimensional coordinate system may be expressed in a three-dimensional table. Moreover, an identifier for the class for a particle of the first classification or an identifier for the class of a particle for the second classification may be assigned in each cell of the three-dimensional table that is specified by the intensities of the first, second, and third lights. The discriminating boundary may be defined by a multivariate function that has the intensities of the first through third lights as variables. A multivariate function may be acquired through a support vector machine.

The particle detecting device set forth above may further includes: a degradation information recording portion for recording degradation information for the light measuring instruments; and a correcting portion for correcting a measured value for the intensity of the first light, the intensity of the second light, and/or the intensity of the third light. Conversely, the particle detecting device set forth above may further include: a degradation information recording portion for recording degradation information for the light measuring instruments; and a correcting portion for correcting the discriminating boundary based on the degradation information.

Another aspect of the present invention provides a particle detecting method including: measuring measured values of intensities of first, second, and third lights, produced by a particle being measured, with mutually varying wavelengths; storing a non-linear discriminating boundary for separating a class of particles of a first classification and a class of particles of a second classification; and classifying a particle to be measured into a class for particles of either a first or second classification, based on the measured values for the intensities for the first through third lights and on a discriminating boundary.

In the particle detecting method set forth above: the first and second lights may be lights in the fluorescent band, and the third light may be scattered light. Moreover, one of the particles of the first and second classifications may be a biologic particle, and the other may be a non-biologic particle.

In the particle detecting method, the discriminating boundary may be included in a three-dimensional coordinate system. Moreover, the three-dimensional coordinate system may be expressed in a three-dimensional table. Furthermore, an identifier for the class for a particle of the first classification or an identifier for the class of a particle for the second classification may be assigned in each cell of the three-dimensional table that is specified by the intensities of the first, second, and third lights. The discriminating boundary may be defined by a multivariate function that has the intensities of the first through third lights as variables. A multivariate function may be acquired through a support vector machine.

The particle detecting method set forth above may further include: measuring measured values for intensities of first, second, and third lights of mutually differing wavelengths, produced by particles to be measured; correcting a measured value for the intensity of the first light, the intensity of the second light, and/or the intensity of the third light. Conversely, the particle detecting method as set forth above may further include: measuring measured values for intensities of first, second, and third lights of mutually differing wavelengths, produced by particles to be measured; and correcting the discriminating boundary based on the degradation information.

The present invention makes it possible to provide a particle detecting device and particle detecting method wherein biologic particles and non-biologic particles can be discriminated accurately.

BRIEF DESCRIPTIONS OF THE DRAWINGS

Figure 3:
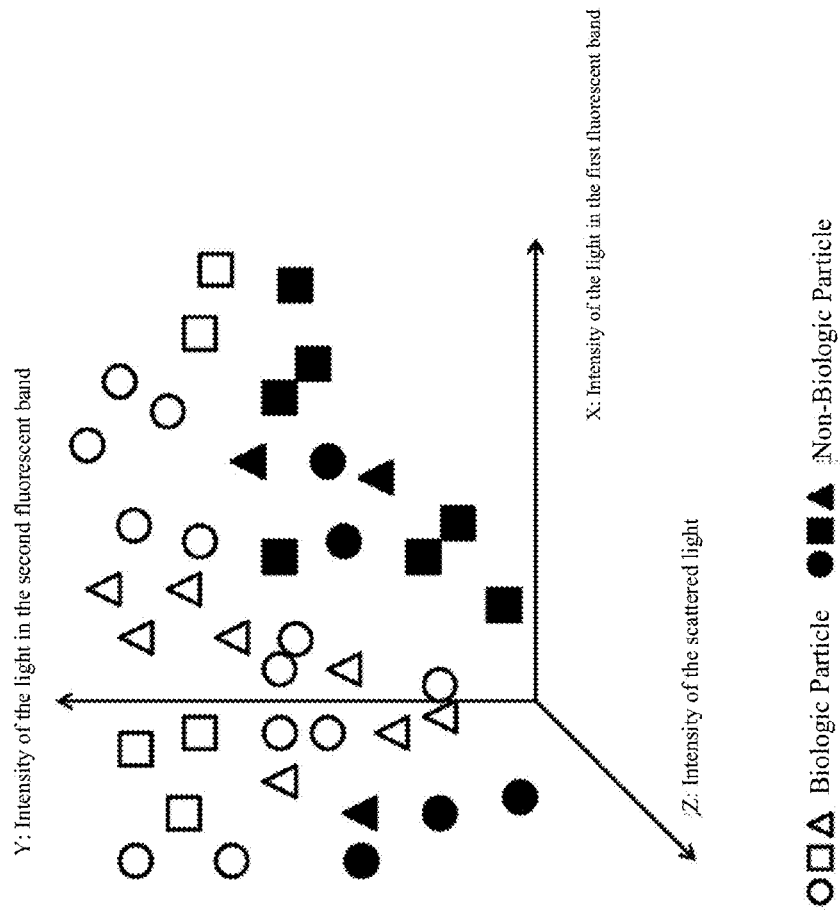

FIG. 3 is a schematic graph, for multiple types of known biologic particles and non-biologic particles, in a three-dimensional coordinate system that includes an x axis, a y axis, and a z axis, for measured values of intensities of light in a first fluorescent band, measured values for intensities of light in a second fluorescent band, and measured values for intensities of scattered light, produced when illuminated with light.

Figure 4:
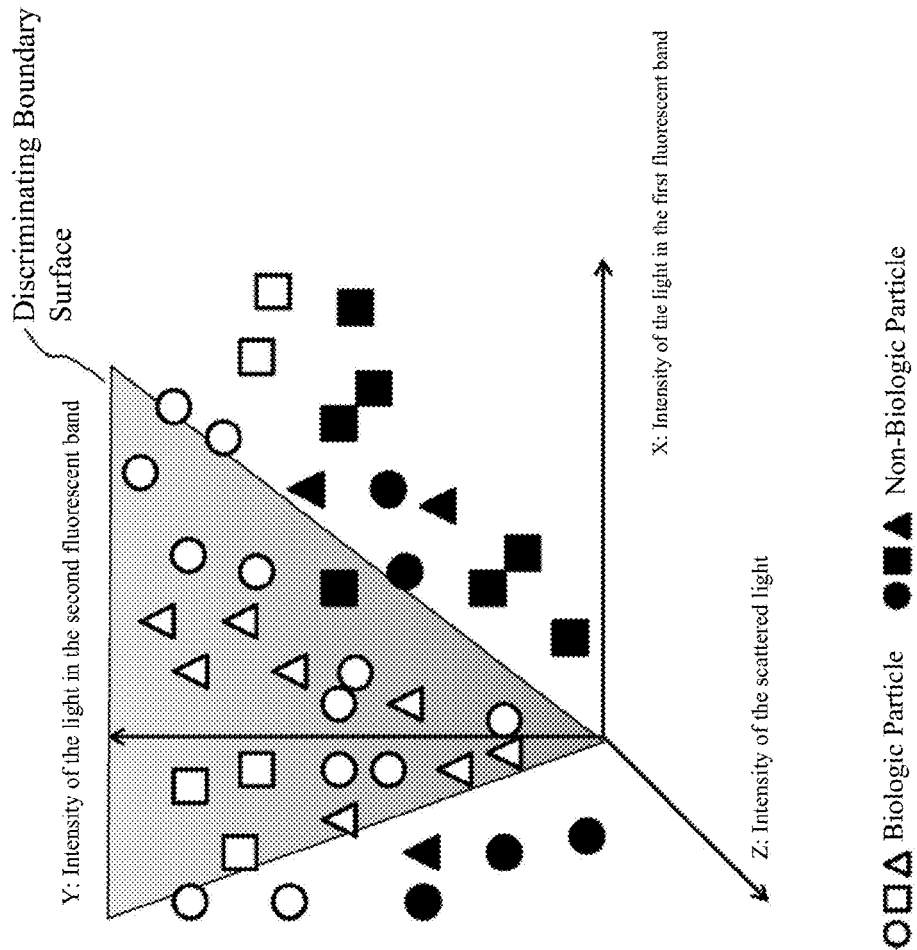

FIG. 4 is a schematic graph wherein a linear discriminating boundary for dividing a class for biologic particles and a class for non-biologic particles has been added to the graph illustrated in FIG. 3.

Figure 5:
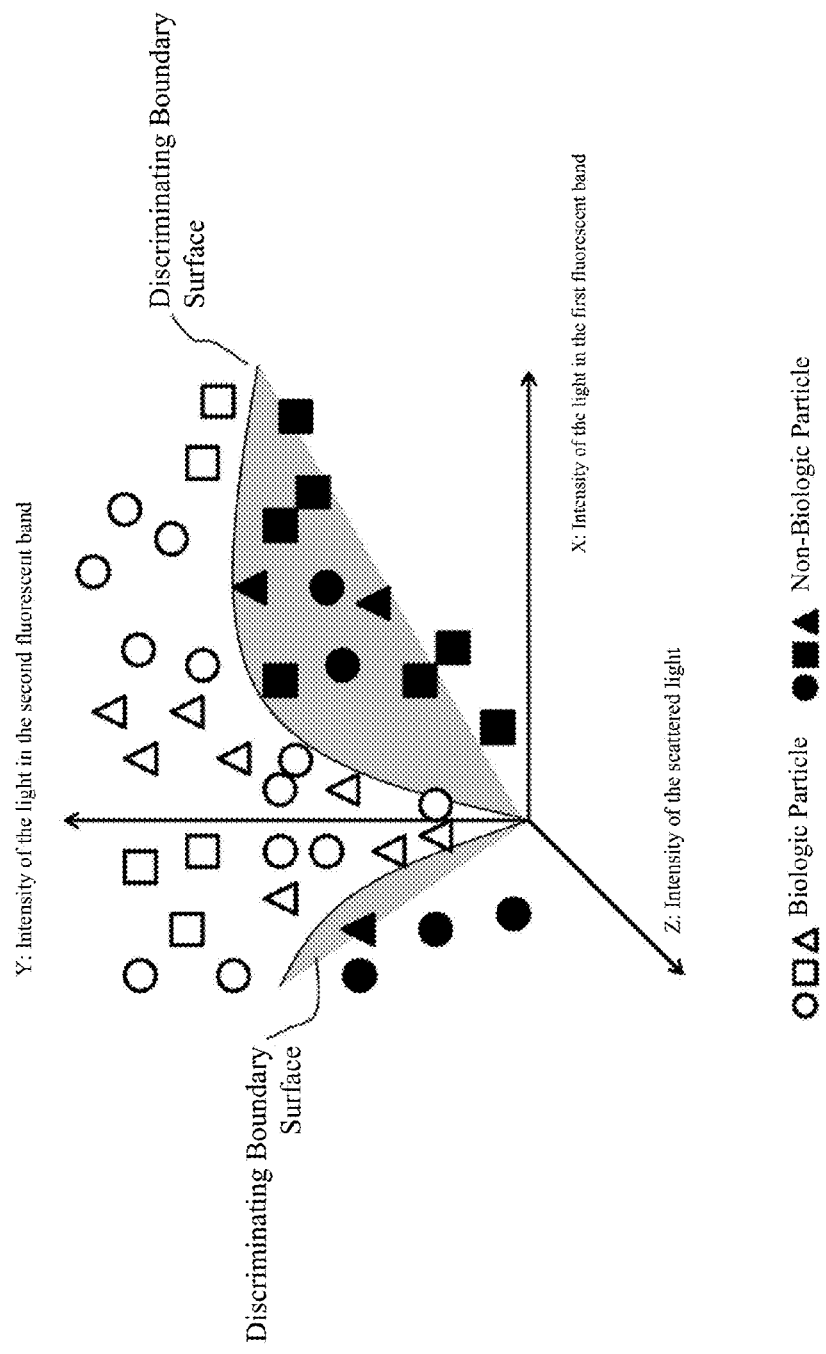

FIG. 5 is a schematic graph wherein a non-linear discriminating boundary for dividing a class for biologic particles and a class for non-biologic particles has been added to the graph illustrated in FIG. 3.

Figure 6:
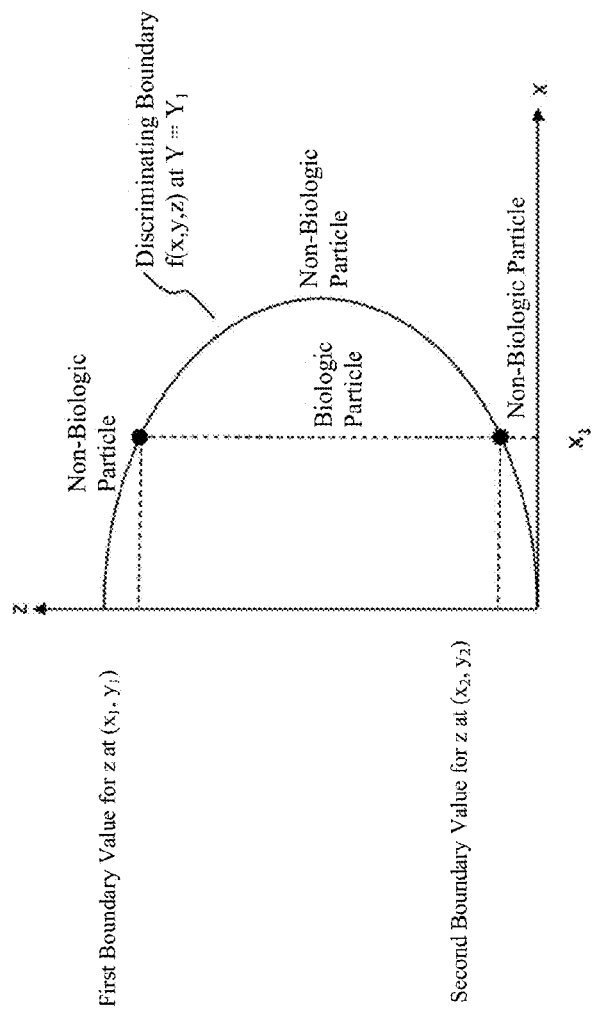

FIG. 6 is a schematic graph of discriminating boundaries in an x-z two-dimensional coordinate system at an arbitrary value for y according to the Example according to the present invention.

Figure 7:
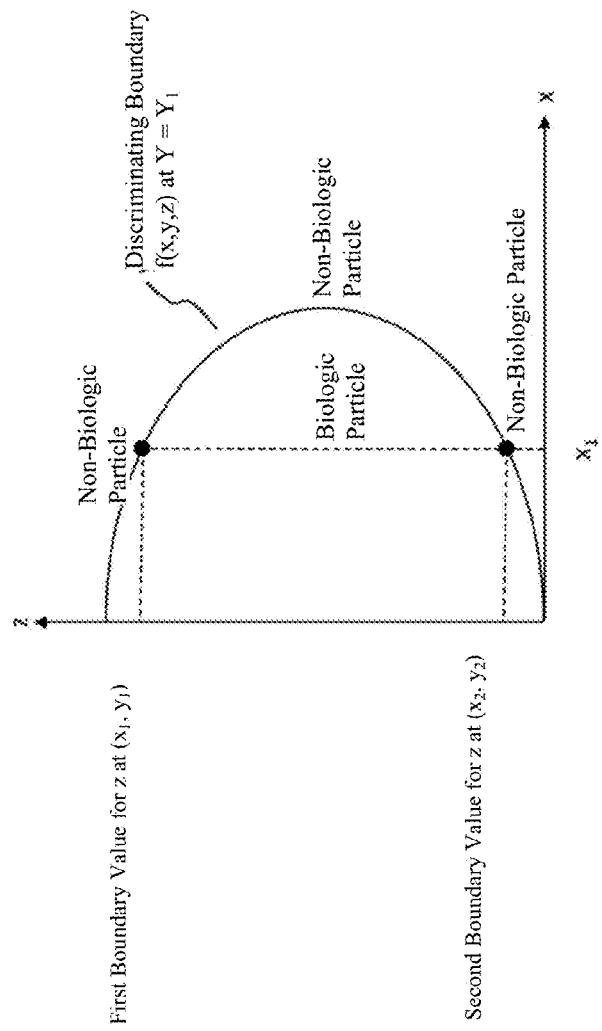

FIG. 7 is a schematic graph of discriminating boundaries in an x-z two-dimensional coordinate system at an arbitrary value for y according to the Example according to the present invention.

Figure 8:
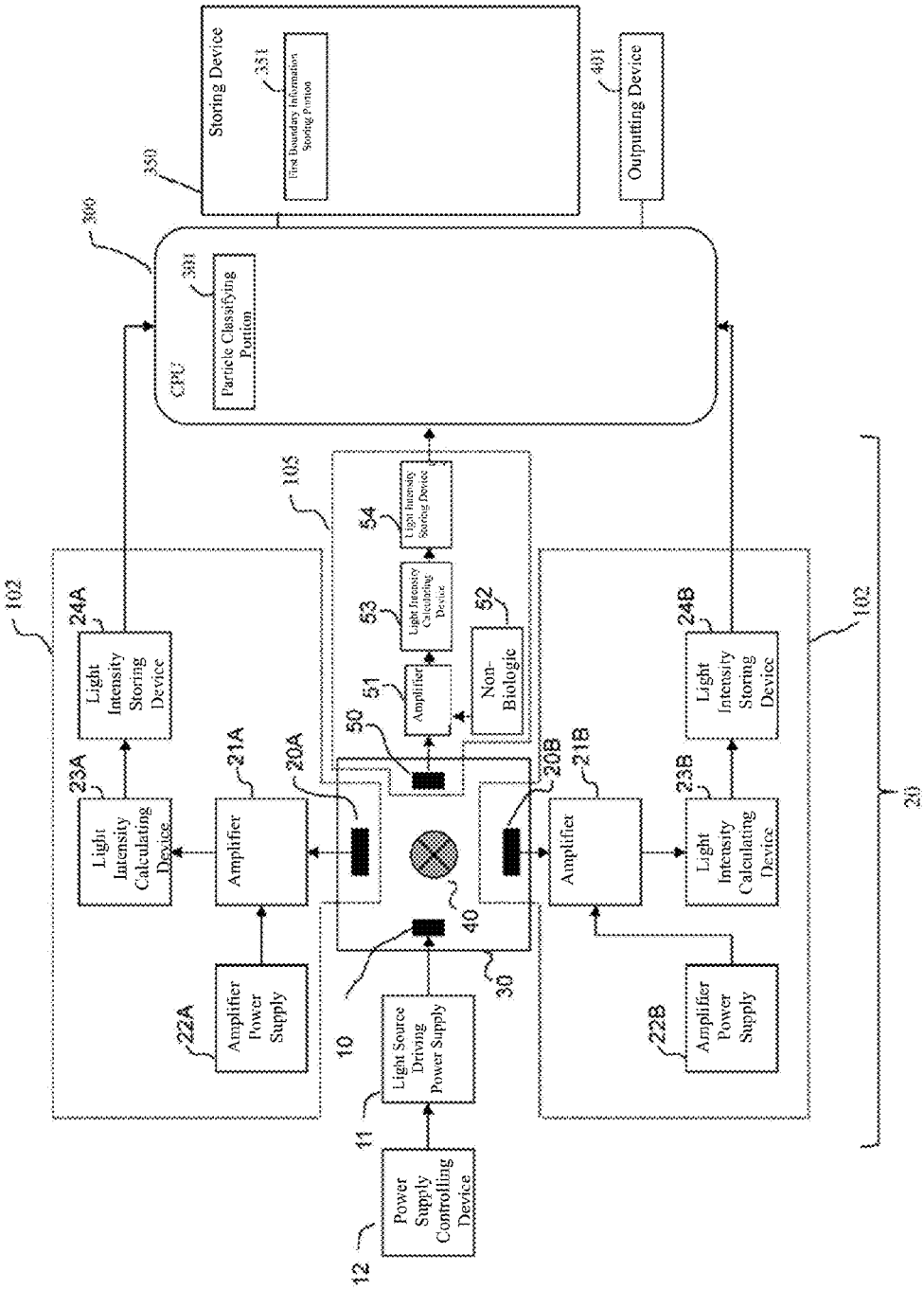

FIG. 8 is a schematic diagram of a detecting device according to the Example according to the present invention.

Figure 9:
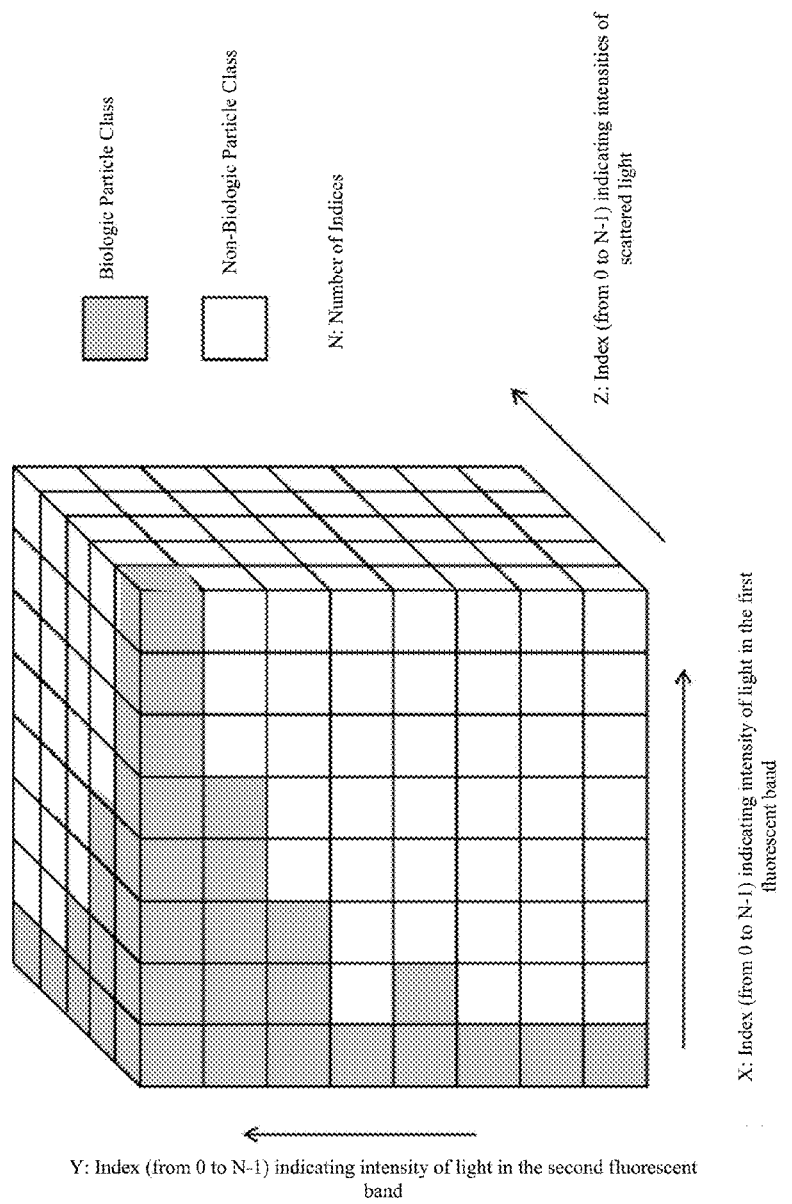

FIG. 9 is a schematic diagram of a three-dimensional table according to the Example according to the present disclosure.

Figure 10:
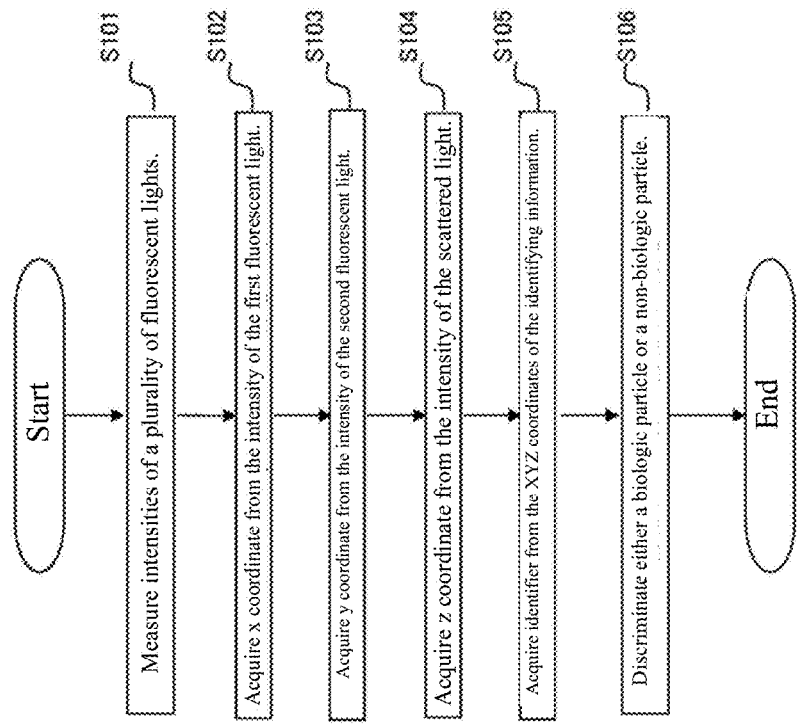

FIG. 10 is a flowchart illustrating the method for detecting particles according to the Example according to the present invention.

Figure 11:
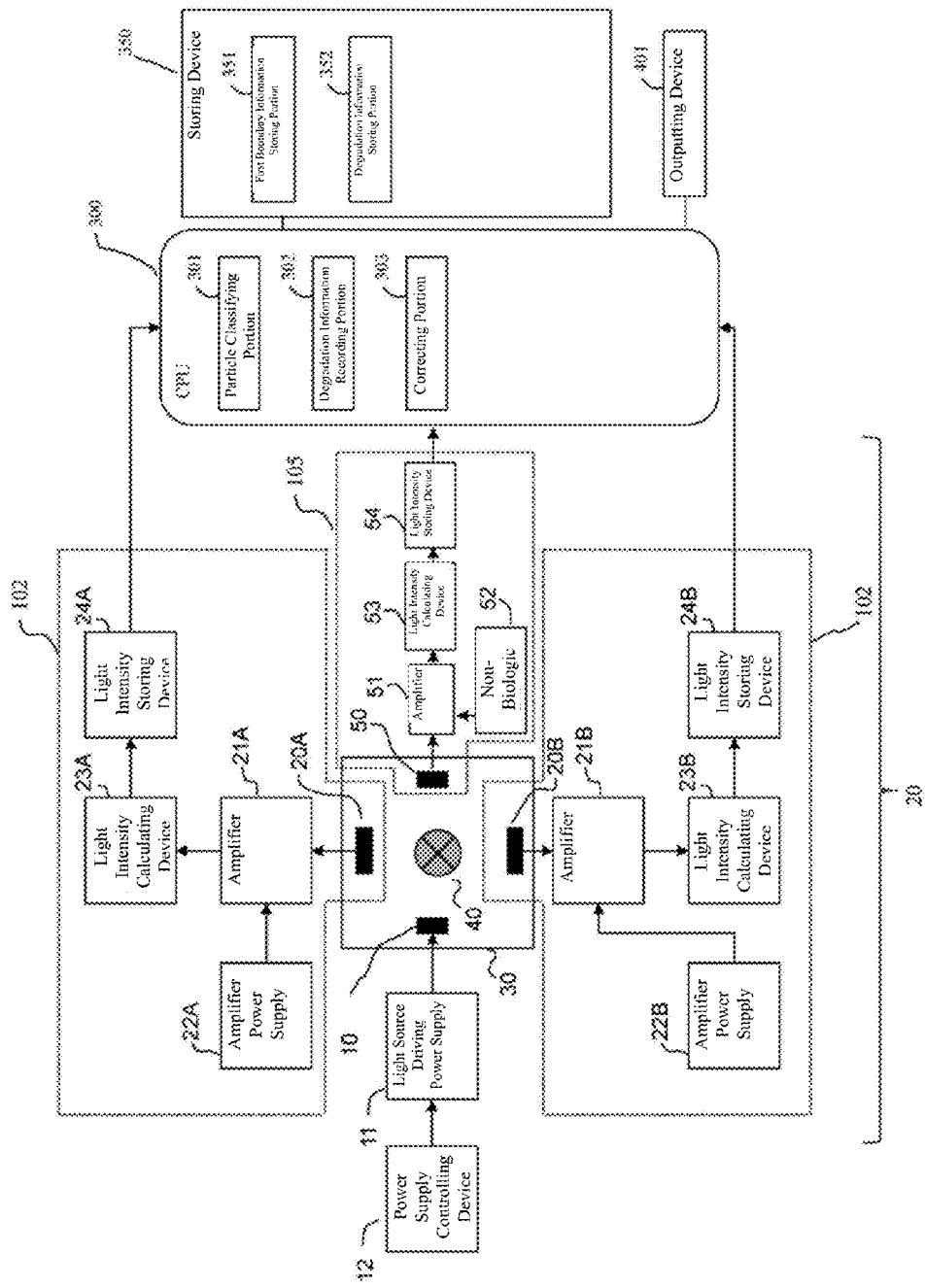

FIG. 11 is a schematic diagram of a detecting device according to Another Example according to the present invention.

DETAILED DESCRIPTION

Examples of the present invention will be described below. In the descriptions of the drawings below, identical or similar components are indicated by identical or similar codes. Note that the diagrams are schematic. Consequently, specific measurements should be evaluated in light of the descriptions below. Furthermore, even within these drawings there may, of course, be portions having differing dimensional relationships and proportions.

EXAMPLE

When a biologic particle, such as a bacterium, is illuminated with light, scattered light is produced at the biologic particle. Moreover, even when a non-biologic particle, such as of metal or a resin, is illuminated with light, scattered light is produced at the non-biologic particle. The intensity of the scattered light produced by a particle tends to be dependent on the size of the particle. The particle diameters of biologic particles are different depending on the type of microorganism. Moreover, the particle diameters of non-biologic particles are also different depending on the type. Because of this, it is possible to identify the type of measured particle that is included in the fluid from the intensity of the scattered light.

Moreover, when a biologic particle is illuminated with an excitation light, the nicotinamide adenine dinucleotide (NADH) and the riboflavin, and the like, that are included in biologic particle produces fluorescent light. Even when the non-biologic particles are illuminated with light, the non-biologic particle may emit light in the fluorescent band. Fluorescent particles that fall off of a polyester gown, for example, that has been cleaned will emit fluorescence when illuminated with light. Polystyrene particles also emit fluorescence, and then fade.

Moreover, when, for example, a gas includes a nitrogen oxide ($NO_x$), including nitrogen dioxide ($NO_2$), a sulfur oxide ($SO_x$), ozone gas ($O_3$), an aluminum oxide gas, an aluminum alloy, a glass powder, or a decontaminating gas for decontaminating *Escherichia coli* or mold contamination, or the like, substances included in the gas, which may be smaller than particles that produce Mie scattering, will absorb the light to produce light in the fluorescent band.

For example, when nitrogen dioxide absorbs gas, light that is shifted in the red direction is emitted when returning to the base state. The absorption spectrum of nitrogen dioxide has a peak at a wavelength of about 440 nm, but has a broad band between about 100 and 200 nm. Because of this, when, in the presence of nitrogen dioxide, there is an attempt to stimulate NADH fluorescence or flavin fluorescence, which has a wavelength of 405 nm, fluorescence will be stimulated in the nitrogen dioxide as well, which overlaps the absorption spectrum of the excitation beam for the NADH and flavin. Moreover, nitrogen dioxide is generated through a reaction of nitrogen and oxygen in the gas when a substance is combusted. Because of this, even if initially there is no nitrogen dioxide in the gas being inspected, when the gas being inspected is illuminated with a laser beam that has a high beam density, or with a strong electromagnetic emission beam as the excitation beam, substances in the gas may combust to produce nitrogen dioxide, where the nitrogen dioxide may produce fluorescence. Moreover, carbon monoxide and ozone react to form nitrogen dioxide, which may produce fluorescence.

In regards to nitrogen dioxide, please reference Japanese Unexamined Patent Application Publication 2003-139707, Joel A. Thornton, et al., "Atmospheric $NO_2$: In Situ Laser-Induced Fluorescence Detection at Parts per Trillion Mixing Ratios," Analytical Chemistry, Vol. 72, No. 3, Feb. 2000, pp. 528-539, and S. A. Nizkorodov, et al., "Time-resolved fluorescence of $NO_2$ in a magnetic field," Volume 215, No. 6, Chemical Physics Letters, 17 Dec. 1993, pp. 662-667. In regards to sulfur oxides, reference Japanese Unexamined Patent Application Publication 2012-86105.

Figure 1:
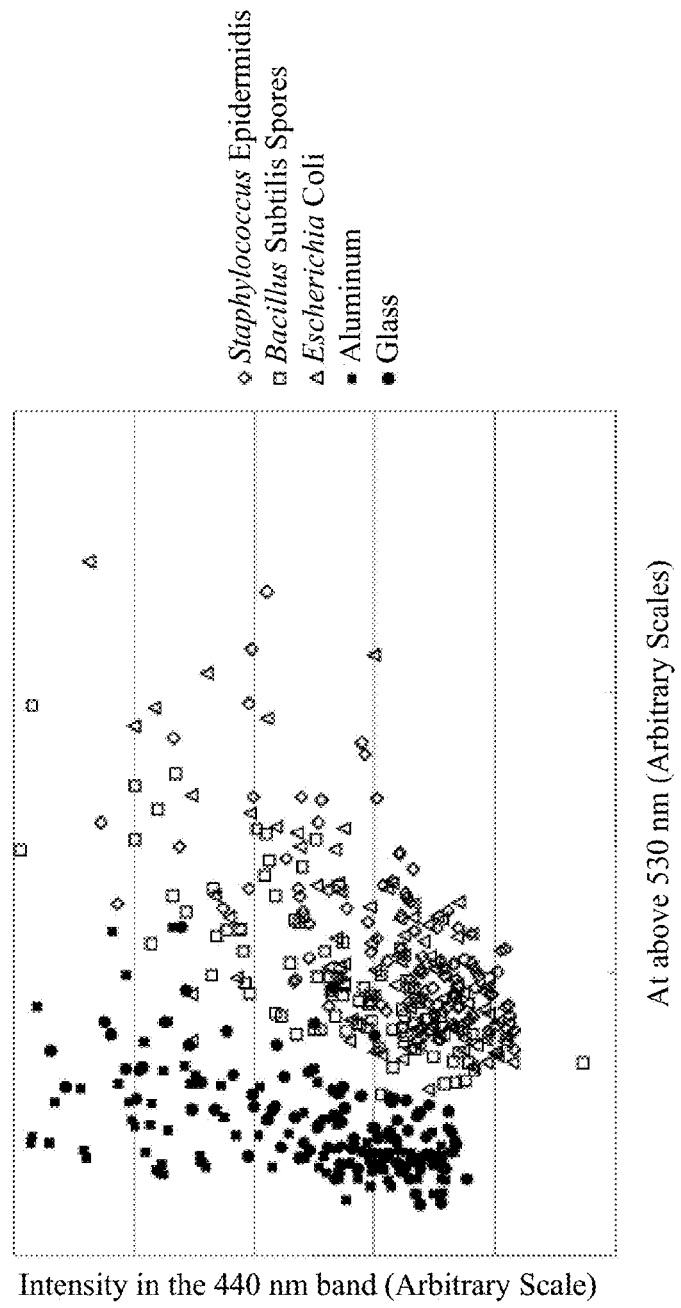
FIG. 1 is a graph showing the relationships of the intensity of light in the 440 nm band, versus the intensity in the band of 530 nm and above, for light emitted from a microorganism and from a substance included in the air in Example according to the present invention.

After diligent research, the present inventors discovered that when the intensities of light in the fluorescent band, emitted by a substance, are measured at the plurality of wavelengths, the correlation of the intensity of light at one wavelength to the intensity of light that another wavelength will vary depending on the individual substance. For example, FIG. 1 is a graph plotting the intensities of light wavelengths in the band above 530 nm, on the horizontal axis, versus the intensity of light at a wavelength in band near to 440 nm, on the vertical axis, for *Staphylococcus epidermidis*, *Bacillus subtilis* spores, *Escherichia coli*, glass, and aluminum, illuminated with an excitation beam. As illustrated in FIG. 1, the ratio of the intensities of light at wavelengths in the band of above 530 nm to the intensities of light of the wavelengths in the band near to 440 nm tends to be small for non-biologics and tends to be large for microorganism particles. In this way, the present inventors discovered that measuring the intensities of light in the fluorescent band, emitted by a substance, at each of a plurality of wavelengths and then taking the correlations makes it possible to identify whether a substance is a biologic or a non-biologic.

Figure 2:
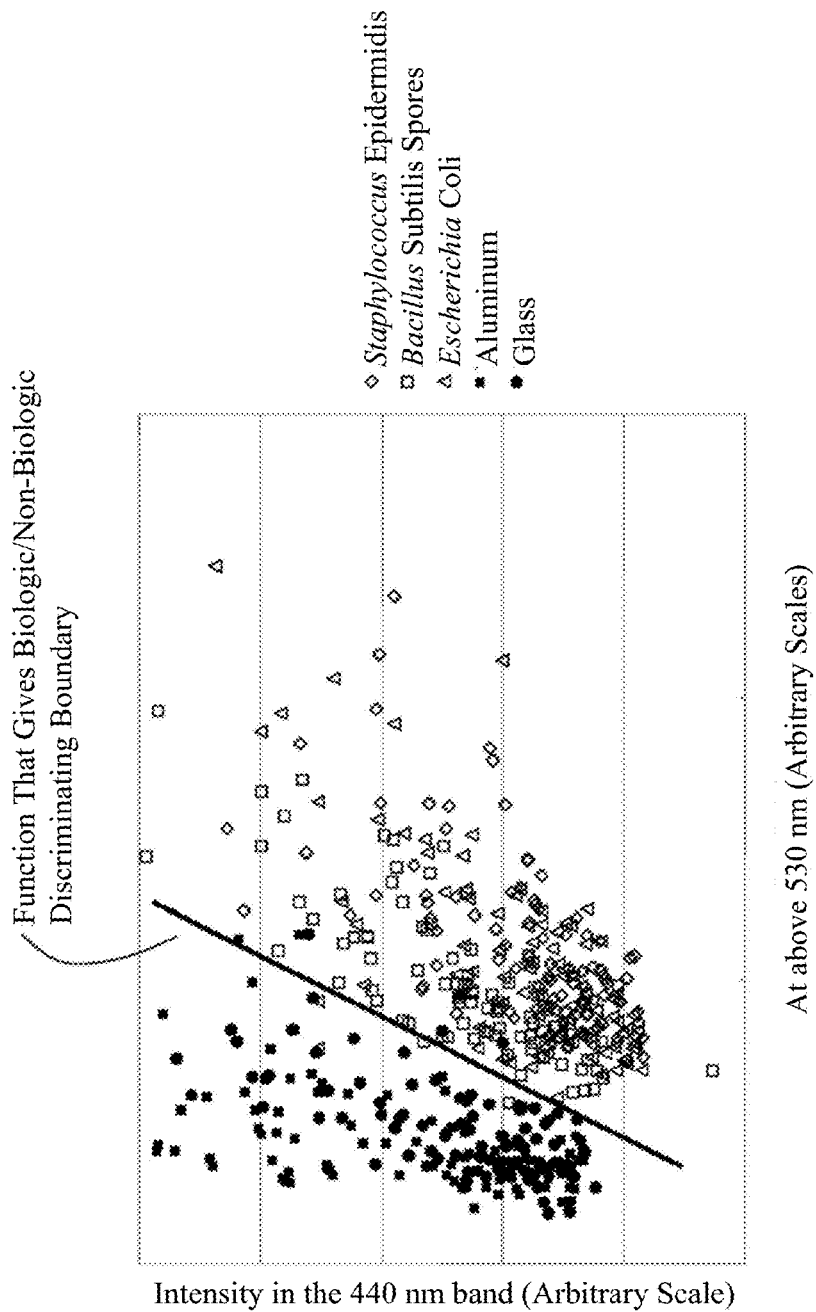
FIG. 2 is a graph showing the relationships of the intensity of light in the 440 nm band, versus the intensity in the band of 530 nm and above, for light emitted from a microorganism and from a substance included in the air in the Example according to the present invention, and the discriminating boundary.

For example, in FIG. 2, when the horizontal axis, which indicates the intensity of light in a first fluorescent band, is defined as the x-axis and the vertical axis, which indicates the intensity of light in a second fluorescent band, is defined as the y-axis, it is possible to define a function $y=f(x)$ that produces a discriminating boundary between biologics and non-biologics. In the example in FIG. 2, particles that yield intensities of light that are plotted in the region of $y>f(x)$ can be classified as non-biologics, and particles that yield intensities of light that are plotted in the region of $y<f(x)$ can be classified as biologics Furthermore, as described above, the intensity of scattered light produced by a particle varies depending on the type of particle. Because of this, it is possible to define a function $f(x,y,z)$ that yields a discriminating boundary between biologics and non-biologics when measured values for intensities of light in a fluorescent band that has a first wavelength, measured values for intensities of light in the fluorescent band having a second wavelength, and the measured values for intensities of scattered light, produced when multiple types of known biologic particles and non-biologic particles are each illuminated with light, are plotted in a three-dimensional coordinate system having the x-axis, the y-axis, and a z-axis that indicates the intensity scattered light, as illustrated in FIG. 3.

Here, when a class for biologic particles and a class for non-biologic particles are divided linearly, as illustrated in FIG. 4, conventionally particles that should be classified into a biologic particle class may be classified as non-biologic particles, and particles that should be classified into the non-biologic particle class may be classified as biologic particles. In contrast, when, as illustrated in FIG. 5, there is non-linear separation into the biologic particle class and the non-biologic particle class, it is possible to reduce cases where, conventionally, particles that should have been classified into the biologic particle class have been classified as non-biologic particles and particles that should have been classified into the non-biologic particle class have been classified as biologic particles.

The function $f(x,y,z)$ that produces the discriminating boundary, that performs non-linear separation between biologics and non-biologics, can be defined through a non-linear identifier, such as a support vector machine (SVM) that calculates the discriminating boundary, from teaching data, so as to maximize the distances between the individual data points. Note that the identifier is known as a classifier or an identifier. Non-linear identifiers are not limited to support vector machines. For example, an identifier may be used instead that uses boosting in order to increase accuracy through a combination of multiple identifiers, a simulated neural network on a computer with calculation characteristics that look like neural functions, a decision tree, a nearest local search, and empirical inference, or the like, may be used.

For example, when, in the particles that are illuminated with light, there are microorganism particles, non-microorganism particles that are larger than the microorganism particles, and non-microorganism particles that are smaller than the microorganism particles, then, in the three-dimensional coordinate system, as illustrated in FIG. 6, for example, the particles that cause the intensities of light that are plotted in the bounded by the function $f(x,y,z)$ that produces the discriminating boundary scan the classified as biologics, and, for example, as illustrated in FIG. 7, the particles that cause the intensities that are plotted on the outside of the space bounded by the function $f(x,y,z)$ can be classified as non-biologics.

In this case, the function $f(x,y,z)$ that provides the discriminating boundary for biologics and non-biologics, in the three dimensional coordinate system, may be defined in advance, and, thereafter, the intensities of light in the fluorescent band that has the first wavelength, light in the fluorescent band that has the second wavelength, and scattered light, produced when unknown particles are illuminated with the first illumination light, are measured, and if the measured values are plotted in the space that is bounded by the function $f(x,y,z)$, it may be evaluated that the particles that have been measured are biologics, and if the measured values are plotted on the outside of the space bounded by the function $f(x,y,z)$, it can be evaluated that the measured particles are non-biologics.

For example, in the case of a multivariate function $f(x,y,z)$ that defines the disseminating boundary being a multivariate function that outputs two values for the dependent variable z for one set of independent variables (x,y), referencing FIG. 6 and FIG. 7, a particle that has the intensities of light in the first and second fluorescent bands for one set of values for $(x_1, y_1)$, and that gives a measured value for the intensity of scattered light that is greater than a first boundary value for the intensity of scattered light at the discriminating boundary is a non-biologic particle. Moreover, a particle that has the intensities of light in the first and second fluorescent bands with the values in one combination of $(x_1,y_1)$, having a measured value for the scattered light intensity that is less than the first boundary value for the intensity of scattered light, and having a measured value for the scattered light intensity that is greater than the second boundary value for the intensity of scattered light in the discriminating boundary, is a biologic particle. Moreover, a particle that has the measured values for the intensities of light in the first and second fluorescent bands with the values in one combination of $(x_1,y_1)$, and having a scattered light intensity that is less than the second boundary value for the intensity of scattered light is a non-biologic particle. However, the shape of the discriminating boundary varies depending on the sample.

Here, the particle detecting device according to the Example according to the present invention, as illustrated in FIG. 8, includes: a light measuring instrument 20 for measuring measured values of an intensity of a first light having a first wavelength, an intensity of a second like having a second wavelength, and an intensity of a third light having a third wavelength; a boundary information storing portion 351 for saving a non-linear discriminating boundary for dividing into a first classification of particles and a second classification of particles; and a particle classifying portion 301 for classifying particles being measured into first and second classifications based on the measured values for the first through third light intensities and on the discriminating boundary.

The particle classifying portion 301 may be, for example, included in a central calculation processing device (CPU) 300. For example, the boundary information setting portion 351 is included in the storing device 350 that is connected to the CPU 300.

The first wavelength, the second wavelength, and the third wavelength are mutually different. An example will be explained below wherein the first and second lights are lights within the fluorescent band and the third light is scattered light. Note that "light of the fluorescent band" includes fluorescence, autofluorescence, and light that, although not necessarily fluorescence, has a wavelength band that overlaps that of fluorescence. Moreover, an example wherein the particle of the first classification is a biologic particle and the particle of the second classification is a non-biologic particle will be explained below.

A fluid that is to be inspected by a particle detecting device as to whether or not particles are included is sprayed from a nozzle 40. An inspecting light of a broadband wavelength from a light source 10 is directed toward the fluid that is sprayed from the nozzle 40. Note that when a liquid is being inspected, the inspecting light of the broadband wavelength from the light source 10 is directed toward a flow cell, or the like, wherein the liquid is flowing. An example wherein the fluid is a gas will be explained below. A light-emitting diode (LED) or a laser, for example, may be used for the light source 10. The wavelength of the inspecting light may be, for example, between 250 and 550 nm. The inspecting light may be a visible light, or may be ultraviolet radiation. If the inspecting light is visible light, then the wavelength of the inspecting light is, for example, in a range between 400 and 550 nm, for example, 405 nm. If the inspecting light is ultraviolet light, then the wavelength of the inspecting light is, for example, in a range between 300 and 380 nm, for example, 340 nm. However, the wavelengths of the inspecting light are not limited thereto. A light source driving power supply 11 for supplying electric power to the light source 10 is connected to the light source 10. A power supply controlling device 12 for controlling the electric power that is supplied to the light source 10 is connected to the light source driving power supply 11.

The light measuring instrument 20 is provided with: a fluorescent intensity measuring instrument 102 for measuring the intensity of light in a first fluorescent band and intensity of light in a second fluorescent band that are produced by a particle that is included in the fluid sprayed from the nozzle 40 and illuminated by the inspecting light; and a scattered light measuring instrument 105 for measuring scattered light produced by the particle being measured, which is illuminated by the inspecting light. The light source 10, the fluorescent intensity measuring instrument 102, and the scattered light measuring instrument 105 are provided on a frame 30. Moreover, the power supply controlling device 12, the fluorescent intensity measuring instrument 102, and the scattered light measuring instrument 105 are connected electrically to the CPU 300.

The fluorescent intensity measuring instrument 102 detects light in the fluorescent band produced by the particles being measured. The fluorescent intensity measuring instrument 102 includes: a first photodetecting element 20A for detecting light of a fluorescent band at a first wavelength; and a second photodetecting element 20B for detecting light of the fluorescent band at a second wavelength that is different from the first wavelength. Note that the first wavelength may have a band. The same is true regarding the second wavelength. Photodiodes, photoelectron tubes, and the like, may be used for the first photodetecting element 20A and the second photodetecting element 20B, and, when light is detected, the optical energy is converted into electrical energy.

An amplifier 21A, for amplifying the current that is produced by the first photodetecting element 20A, is connected to the first photodetecting element 20A. An amplifier power supply 22A, for supplying electric power to the amplifier 21A, is connected to the amplifier 21A. Moreover, a light intensity calculating device 23A, for calculating the intensity of light detected by the first photodetecting element 20A, by detecting the current that has been amplified by the amplifier 21A, is connected to the amplifier 21A. A light intensity storing device 24A, for storing the intensity of light calculated by the light intensity calculating device 23A, is connected to the light intensity calculating device 23A.

An amplifier 21B, for amplifying the current that is produced by the second photodetecting element 20B, is connected to the second photodetecting element 20B. An amplifier power supply 22B, for supplying electric power to the amplifier 21B, is connected to the amplifier 21B. Moreover, a light intensity calculating device 23B, for calculating the intensity of light detected by the second photodetecting element 20B, by detecting the current that has been amplified by the amplifier 21B, is connected to the amplifier 21B. A light intensity storing device 24B, for storing the intensity of light calculated by the light intensity calculating device 23B, is connected to the light intensity calculating device 23B.

The scattered light measuring instrument 105 detects scattered light produced by a particle being measured, which is illuminated by the inspecting light. The scattered light measuring instrument 105 includes a scattered light photodetecting element 50 for detecting scattered light. A photodiode, or the like, may be used for the scattered light photodetecting element 50, to convert light energy into electrical energy when light is detected.

An amplifier 51 for amplifying the current produced by the scattered light photodetecting element 50 is connected to the scattered light photodetecting element 50. An amplifier power supply 52 for supplying electric power to the amplifier 51 is connected to the amplifier 51. Moreover, a light intensity calculating device 53 for calculating the intensity of the scattered light detected by the scattered light photodetecting element 50 by detecting the current that is amplified by the amplifier 51 is connected to the amplifier 51. A light intensity storing device 54 for storing the intensity of the scattered light that is calculated by the light intensity actuating device 53 is connected to the light intensity calculating device 53.

The discriminating boundary that is stored in the boundary information storing portion 351 is, for example, defined as a multivariate function that has, as variables, intensity of light in the first fluorescent band, intensity of light in the second fluorescent band, and intensity of scattered light. The boundary information storing portion 351 stores, for example, a three-dimensional coordinate system that includes the multivariate function. The three-dimensional coordinate system includes an x coordinate that indicates the intensity of light in the first fluorescent band, a y coordinate that indicates the intensity of light in the second fluorescent band, and a z coordinate that indicates the intensity of scattered light. The three-dimensional coordinate system is expressed as a three-dimensional table including N x N x N cells, with N as an integer, as illustrated in FIG. 9, for example. In this case, for example, the cells in the x direction are assigned indices from 0 to N−1, the cells in the y direction are assigned indices from 0 to N−1, and the cells in the z direction are assigned indices from 0 to N−1.

When, for example, the three-dimensional table is comprised of 256 x 256 x 256 cells, the cells in the x direction are assigned indices from 0 to N−1, the cells in the y direction are assigned indices from 0 to N−1, and the cells in the z direction are assigned indices from 0 to N−1.

The intensity of light is expressed as a voltage signal within a range of, for example, between 0 and 5 V, or the like. The following Equation (1), for example, is used in converting the light intensity into a discrete index I:

$$I = [NIx\ (SD/SM)] \quad (1)$$

Here NI is the number of indices, for example, 256. SD is a measured value for the intensity of the light, expressed as a voltage signal. SM is the maximum value that can be assumed by the light intensity that is expressed as the voltage signal.

The index I, calculated by Equation (1) is an integer number between 0 and 255.

An identifier for the biologic particle class is assigned to each cell that is included in the region for the biologic particle class that is demarcated by the multivariate function that divides the biologic particle class and the non-biologic particle class. Moreover, an identifier for the non-biologic particle class is assigned to each cell that is included in the region for the non-biologic particle class that is demarcated by the multivariate function that divides the biologic particle class and the non-biologic particle class. Additionally, [TRADOS previous sentence] Consequently, specifying a cell for an (x,y,z) coordinate of the three-dimensional table makes it possible to acquire the identifier for the biologic particle class or the non-biologic particle class from a specified cell.

The particle classifying portion 301 illustrated in FIG. 8 uses, for example, Equation (1), above, to specify a cell at a coordinate (x,y,z) in the three-dimensional table that is stored in the boundary information storing portion 351, corresponding to the measured value for the intensity of light in the first fluorescent band, the measured value of the intensity of light in the second fluorescent band, and the measured value for the intensity of scattered light, produced by a particle being measured. Furthermore, if the identifier in the cell at the specify coordinate (x,y,z) is of the biologic particle class, then the particle classifying portion 301 classifies a particle being measured into the biologic particle class. Furthermore, if the identifier in the cell at the specify coordinate (x,y,z) is of the non-biologic particle class, then the particle classifying portion 301 classifies a particle being measured into the non-biologic particle class.

An outputting device 401 is connected to the CPU 300. The outputting device 401 outputs the result of classification by the particle classifying portion 301. A display, a printer, an audio device, or the like, may be used for the outputting device 401.

A particle detecting method according to the Example will be explained next, referencing the flowchart illustrated in FIG. 10.

In Step S101, a flow of gas is sprayed from the nozzle 40, illustrated in FIG. 8. Moreover, an inspecting light is directed toward the gas flow from the light source 10. When a particle is included in the gas flow, scattered light is produced at the particle that is illuminated by the inspecting light. Moreover, the particle that is illuminated by the inspection light emits light in first and second fluorescent bands. The scattered light is detected by a scattered light photodetecting element 50. The light of the first fluorescent band is detected by the first photodetecting element 20A, and the light of the second fluorescent band is detected by the second photodetecting element 20B.

In Step S102, the particle classifying portion 301 uses Equation (1), above, to convert the measured value for the intensity of light in the first fluorescent band into an index. The index that indicates the measured value for the intensity of light in the first fluorescent band corresponds to the x coordinate in the three-dimensional table. In Step S103, the particle classifying portion 301 uses Equation (1), above, to convert the measured value for the intensity of light in the second fluorescent band into an index. The index that indicates the measured value for the intensity of light in the second fluorescent band corresponds to the y coordinate in the three-dimensional table. In the Step S104, the particle classifying portion 301 uses Equation (1) to convert the measured value for the intensity of scattered light into an index. The index that indicates the measured value for the intensity of scattered light corresponds to the z coordinate in the three-dimensional table.

In Step S105, the particle classifying portion 301 reads out the three-dimensional table from the boundary information storing portion 351. Following this, the particle classifying portion 301 reads out, from the three-dimensional table, the identifier at the coordinates (x,y, z) corresponding to the measured values for the intensities of light in the first and second fluorescent bands and the measured value for the intensity of scattered light. When the identifier for a biologic particle class is read out from the three-dimensional table, then, in Step S106, the particle classifying portion 301 classifies the detected particle the measured into a biologic particle class. When the identifier for a non-biologic particle class is read out from the three-dimensional table, then, in Step S106, the particle classifying portion 301 classifies the detected particle the measured into a non-biologic particle class. Moreover, the particle classifying portion 301 outputs the particle classification evaluation result to the outputting device 401.

The particle detecting device according to the Example, set forth above, enables high accuracy classification of particles being measured based on a non-linear discriminating boundary for separating into a biologic particle class and a non-biologic particle class.

Another Example

A particle detecting device according to Another Example according to the present invention, as illustrated in FIG. 11, further includes: a degradation information recording portion 302 for recording degradation information for the light measuring instrument 20; and a correcting portion 303 for correcting, based on the degradation information, the measured value for the intensity of the first light of the first wavelength, the measured value for the intensity of the second light of the second wavelength, and/or the measured value for the intensity of the third light of the third wavelength.

For example, over time the scattered light photodetecting element 50, the first photodetecting element 20A, and the second photodetecting element 20B of the light measuring instrument 20 may experience degradation so that the detection sensitivity thereof is reduced. The degradation information recording portion 302 records, and stores in the degradation information storing portion 352 of the storing device 350, the elapsed time that has elapsed since the particle detecting device was shipped from the factory, the total time over which the particle detecting device has operated, the total time over which the first photodetecting element 20A and the second photodetecting element 20B have each detected light, and the like, as degradation information.

The correcting portion 303 reads out the degradation information from the degradation information storing portion 352. For example, if the degradation information is a record of the total amount of time over which light has been detected by the scattered light photodetecting element 50, the first photodetecting element 20A, and the second photodetecting element 20B, respectively, then the correcting portion 303 increases the values by multiplying by a coefficient, depending on the respective total time over which light has been detected, the measured value for the intensity of light in the first fluorescent band, the measured value for the intensity of light in the second fluorescent band, and the measured value for the intensity of scattered light.

Conversely, the correcting portion 303 may correct the three-dimensional coordinate system that includes the discriminating boundary, stored in the boundary information storing portion 351, based on degradation information. Specifically, the correcting portion 303 may reduce the x coordinate of the three-dimensional coordinate system by multiplying with a coefficient in accordance with the reduction in photodetecting sensitivity of the first photodetecting element 20A. Conversely, the correcting portion 303 may reduce the y coordinate of the three-dimensional coordinate system by multiplying with a coefficient in accordance with the reduction in photodetecting sensitivity of the second photodetecting element 20B. Conversely, the correcting portion 303 may reduce the z coordinate of the three-dimensional coordinate system by multiplying with a coefficient in accordance with the reduction in photodetecting sensitivity of the scattered light photodetecting element 50.

The particle detecting device according to the Another Example enables extended high precision discrimination of particles even given the occurrence of degradation in the light measuring instrument 20.

Other Examples

While there are descriptions of examples as set forth above, the descriptions and drawings that form a portion of the disclosure are not to be understood to limit the present disclosure. A variety of alternate examples and operating technologies should be obvious to those skilled in the art. For example, while explanations were for an example wherein the first and second lights are lights in the fluorescent band and the third light is scattered light, the wavelengths for the first through third lights are arbitrary, insofar as they are mutually different. Moreover, while explanations were for an example where in the particle of the first classification was a biologic particle and the particle of the second classification was a non-biologic particle, instead the particle of the first classification may be a given type of biologic particle and the particle of the second classification may be another type of biologic particle. Conversely, the particle of the first classification may be one type non-biologic particle, and the particle of the second classification may be another type of non-biologic particle. The method of classifying the particles is arbitrary. In this way, the present disclosure should be understood to include a variety of examples, and the like, not set forth herein.

The invention claimed is:

1. A particle detecting device comprising:
   a light measuring instrument that measures measured values for intensities of first, second, and third lights of mutually differing wavelengths, produced by particles to be measured;
   a boundary information storing portion that stores a non-linear discriminating boundary for separating a class of a first classification of particles and a class of a second classification of particles; and
   a particle classifying portion that classifies the particle being measured into either of the classifications for the first and second classifications of particles, based on measured values for the intensities of the first through third lights and on the discriminating boundary.

2. The particle detecting device as set forth in claim 1, wherein:
   the first and second lights are lights in the fluorescent band, and the third light is scattered light.

3. The particle detecting device as set forth in claim 1, wherein:
   one of the particles of the first and second classifications is a biologic particle, and the other is a non-biologic particle.

4. The particle detecting device as set forth in claim 1, wherein:
   the boundary information storing portion also stores a three-dimensional coordinate system wherein the discriminating boundary is defined in three dimensions relative to the three-dimensional coordinate system.

5. The particle detecting device as set forth in claim 4, wherein:
   the three-dimensional coordinate system is expressed in a three-dimensional table.

6. The particle detecting device as set forth in claim 5, wherein:
   an identifier for the class for a particle of the first classification or an identifier for the class of a particle for the second classification is assigned in each cell of the three-dimensional table that is specified by the intensities of the first, second, and third lights.

7. The particle detecting device as set forth in claim 1, wherein:
   the discriminating boundary is defined by a multivariate function that has the intensities of the first through third lights as variables.

8. The particle detecting device as set forth in claim 7, wherein:
   a multivariate function is acquired through a support vector machine.

9. The particle detecting device as set forth in claim 1, further comprising:
   a degradation information recording portion that records degradation information for the light measuring instrument comprising particle detecting device history data; and
   a correcting portion that corrects a measured value for the intensity of the first light, the intensity of the second light, and/or the intensity of the third light by calculating a corrected value using the measured value and a coefficient based on the degradation information.

10. The particle detecting device as set forth in claim 1, further comprising:
  a degradation information recording portion that records degradation information for the light measuring instrument comprising particle detecting device history data; and
  a correcting portion that corrects the discriminating boundary by a calculating at least one corrected coordinate of the three-dimensional coordinate system using the three-dimensional coordinate system and a coefficient based on the degradation information.

11. A particle detecting method, including:
  measuring measured values for intensities of first, second, and third lights of mutually differing wavelengths, produced by particles to be measured;
  preparing a non-linear discriminating boundary for separating a class of a first classification of particles and a class of a second classification of particles; and
  classifying the particle being measured into either of the classifications for the first and second classifications of particles, based on measured values for the intensities of the first through third lights and on the discriminating boundary.

12. The particle detecting method as set forth in claim 11, wherein:
  the first and second lights are lights in the fluorescent band, and the third light is scattered light.

13. The particle detecting method as set forth in claim 11, wherein:
  one of the particles of the first and second classifications is a biologic particle, and the other is a non-biologic particle.

14. The particle detecting method as set forth in claim 11, wherein:
  the discriminating boundary is defined in three dimensions relative to a three-dimensional coordinate system.

15. The particle detecting method as set forth in claim 14, wherein:
  the three-dimensional coordinate system and the discriminating boundary are expressed in a three-dimensional table comprising a plurality of points defined by first, second, and third coordinates.

16. The particle detecting method as set forth in claim 15, wherein:
  an identifier for the class for a particle of the first classification or an identifier for the class of a particle for the second classification is assigned in each cell of the three-dimensional table that is specified by the intensities of the first, second, and third lights.

17. The particle detecting method as set forth in claim 11, wherein:
  the discriminating boundary is defined by a multivariate function that has the intensities of the first through third lights as variables.

18. The particle detecting method as set forth in claim 17, wherein:
  a multivariate function is acquired through a support vector machine.

19. The particle detecting method as set forth in claim 11, further including:
  correcting a measured value for the intensity of the first light, the intensity of the second light, and/or the intensity of the third light by a calculating a corrected value using the measured value and a coefficient based on degradation information comprising particle detecting device history data.

20. The particle detecting method as set forth in claim 11, further including:
  correcting the discriminating boundary based on degradation information comprising particle detecting device history data by calculating a corrected coordinate of the three-dimensional coordinate system using the three-dimensional coordinate system and a coefficient based on the degradation information.

* * * * *